(12) United States Patent
Arai et al.

(10) Patent No.: US 7,979,943 B2
(45) Date of Patent: Jul. 19, 2011

(54) CLEANING BRUSH

(75) Inventors: Keiichi Arai, Tokyo (JP); Motohiro Kuroda, Tokyo (JP)

(73) Assignee: Olympus Corporation, Tokyo (JP)

( * ) Notice: Subject to any disclaimer, the term of this patent is extended or adjusted under 35 U.S.C. 154(b) by 860 days.

(21) Appl. No.: 11/793,564

(22) PCT Filed: Dec. 1, 2005

(86) PCT No.: PCT/JP2005/022108
§ 371 (c)(1),
(2), (4) Date: Jun. 19, 2007

(87) PCT Pub. No.: WO2006/067942
PCT Pub. Date: Jun. 29, 2006

(65) Prior Publication Data
US 2008/0141473 A1    Jun. 19, 2008

(30) Foreign Application Priority Data
Dec. 24, 2004    (JP) .................................. 2004-374277

(51) Int. Cl.
B08B 9/04    (2006.01)
A46B 5/06    (2006.01)

(52) U.S. Cl. .................................. 15/104.05; 15/104.2

(58) Field of Classification Search ............... 15/104.05, 15/104.16, 104.2, 104.33, 206
See application file for complete search history.

(56) References Cited

U.S. PATENT DOCUMENTS

| | | | |
|---|---|---|---|
| 4,733,425 A * | 3/1988 | Hartel et al. .................... | 15/206 |
| 5,038,509 A | 8/1991 | Stephan | |
| 5,168,593 A | 12/1992 | Poje et al. | |
| 5,297,310 A | 3/1994 | Cox et al. | |
| 5,964,004 A | 10/1999 | Bean | |
| 6,299,371 B1 | 10/2001 | Gueret | |
| 6,725,492 B2 * | 4/2004 | Moore et al. ................. | 15/104.2 |
| 2001/0016962 A1 | 8/2001 | Moore et al. | |
| 2004/0031114 A1 | 2/2004 | Dragan et al. | |

FOREIGN PATENT DOCUMENTS

| | | |
|---|---|---|
| GB | 2 294 222 A | 4/1996 |
| JP | 61-111334 | 7/1986 |
| JP | 62-30806 | 2/1987 |
| JP | 63-79738 | 5/1988 |

(Continued)

OTHER PUBLICATIONS

European Office Action dated Dec. 13, 2010.

*Primary Examiner* — Shay L Karls
(74) *Attorney, Agent, or Firm* — Scully, Scott, Murphy & Presser, P.C.

(57) ABSTRACT

A cleaning brush which is inserted into a conduit of the endoscope, includes a long and flexible shaft, and a brush part provided at a leading end of the shaft. The brush part includes brush bristles, a strand, etc. A part of the shaft that overlaps the brush bristles in a state where the brush bristles are bent toward the leading end of the shaft, is provided with a small diameter part that is smaller in external diameter than the other part of the shaft. The dimension obtained by adding the external diameter of the small diameter part and twice the external diameter of the brush bristles is smaller than the internal diameter of a conduit into which this cleaning brush is inserted.

7 Claims, 10 Drawing Sheets

FOREIGN PATENT DOCUMENTS

| | | |
|---|---|---|
| JP | 7-299080 | 11/1995 |
| JP | 9-187421 | 7/1997 |
| JP | 11-169334 | 6/1999 |
| JP | 2001-275962 | 10/2001 |
| JP | 2002-209848 | 7/2002 |
| JP | 2004-208961 | 7/2004 |
| JP | 2004-350966 | 12/2004 |
| WO | WO 02/07559 A2 | 1/2002 |

* cited by examiner

CLEANING BRUSH

TECHNICAL FIELD

The present invention relates to a cleaning brush to be used, for example, when conduits of an endoscope, etc. are cleaned.

Priority is claimed on Japanese Patent Application No. 2004-374277, filed Dec. 24, 2004, the content of which is incorporated herein by reference.

BACKGROUND ART

Fluid conduits, such as a suction conduit and a water feed or air feed conduit, are provided in an endoscope for the purpose of ensuring a field of view when the inside of a body cavity is observed. When endoscopic inspection or trans-endoscopic operation is performed, a patient's blood, mucus, secretion, etc. may pass through such conduits. Further, these liquids may flow back to and enter a conduit from an opening at a leading end of the endoscope, or these liquids may remain in a conduit even after inspection. For this reason, liquids adhering to the internal wall of a conduit are cleaned by a cleaning brush for the endoscope.

The cleaning brush for the endoscope is composed of a long and flexible shaft to be inserted into a conduit of the endoscope, and a brush part provided at a leading end of the shaft. Although the internal diameter of conduits of an endoscope varies depending on types of endoscopes or types of conduits, it takes time and effort to use a plurality of different brushes according to internal diameters. Thus, conduits having various diameters are cleaned by using one brush capable of cleaning conduits ranging from a conduit having a maximum diameter to a conduit having a minimum diameter.

A conventional cleaning brush 100 is shown in FIG. 11. As for a brush part 101 of this cleaning brush 100, a plurality of resinous brush bristles 102 are arranged, and then, interposed, and twisted between metallic strands 103, whereby the brush bristles 102 are planted so as to form a cylindrical shape as a whole. A leading tip 104 made of resin is attached to a leading end of the brush part 101. A trailing end of the strand 103 is fixed to a shaft 105 by being screwed into a leading end of the shaft. Further, Patent Document 1 described below discloses a cleaning brush for an endoscope having a linear support made of a single wire, and a brush part provided at a trailing end of the linear support.

Patent Document 1: Japanese unexamined patent application, First Publication, No. 11-169334

When the conventional cleaning brush 100 shown in FIG. 11 is inserted into a conduit 106 having a small internal diameter close to the external diameter of the shaft 105, the brush bristles 102 are bent down along the internal wall of the conduit 106. For this reason, some of the brush bristles 102 are bent toward a side face of the leading end of the shaft 105, and then overlap the side face of the leading end of the shaft 105. The external diameter of this overlapping portion has a maximum value obtained by adding the external diameter of the shaft 105 and twice the external diameter of the brush bristles 102. This value may exceed the internal diameter of the conduit 106. If the cleaning brush 100 continues to be inserted in such a state, problems occur in that insertion is not allowed and insertion resistance is large.

If the shaft 105 is made thin in order to prevent the above problems, the strength of the shaft 105 declines, and when the shaft 105 is gripped and inserted into the conduit 106, the shaft 105 is apt to be buckled. Further, when the shaft 105 is gripped and inserted by a person's fingers, a problem occurs in that the contact area between the shaft 105 and the fingers may become small, and the fingers are apt to slip.

If the brush bristles 102 are made thin in order to prevent the above problem, a repulsive force when the brush bristles 102 hit the internal wall of the conduit 106 will decrease, and the capability of removing stains will decline.

In order to keep the brush bristles 102 from overlapping the side face of the shaft 105 even if the brush bristles 102 are bent, increasing the distance between the leading face of the shaft 105 and the brush bristles 102 is also conceivable. However, the strand 103 which fixes the brush bristles 102 is hard compared to the flexible shaft 105. When the length of this hard part increases, there is a problem in that it is difficult to pass the brush part 101 through endoscope conduits 106 which are complicated and have a small radius of curvature.

DISCLOSURE OF INVENTION

Therefore, the invention provides a cleaning brush capable of being used for cleaning various conduits of an endoscope, etc., and capable of preventing an increase in resistance or insertion from being disabled, when the cleaning brush is inserted into a conduit.

The invention provides a cleaning brush which is inserted into a conduit to be cleaned, including a long and flexible shaft, and a brush part provided at a leading end of the shaft, and having brush bristles for cleaning the inside of a conduit. The shaft includes a small diameter part smaller in external diameter than other part of the shaft, and the small diameter part is located at a portion overlapped with the brush bristles bent toward the leading end of the shaft.

In a preferable embodiment of the invention, the small diameter part has an external diameter Ds, one of the brush bristles has an external diameter Db, and the conduit has an internal diameter Dk which satisfy the formula: $Ds+Db \times 2 \leq Dk$.

Further, an example of the shape of the small diameter part is taper in which the external diameter of the small diameter part decreases toward the leading face of the shaft.

BEST MODE FOR CARRYING OUT THE INVENTION

Hereinafter, a cleaning brush according to a first embodiment of the invention will be described with reference to FIGS. 1 to 3.

Figure 1:
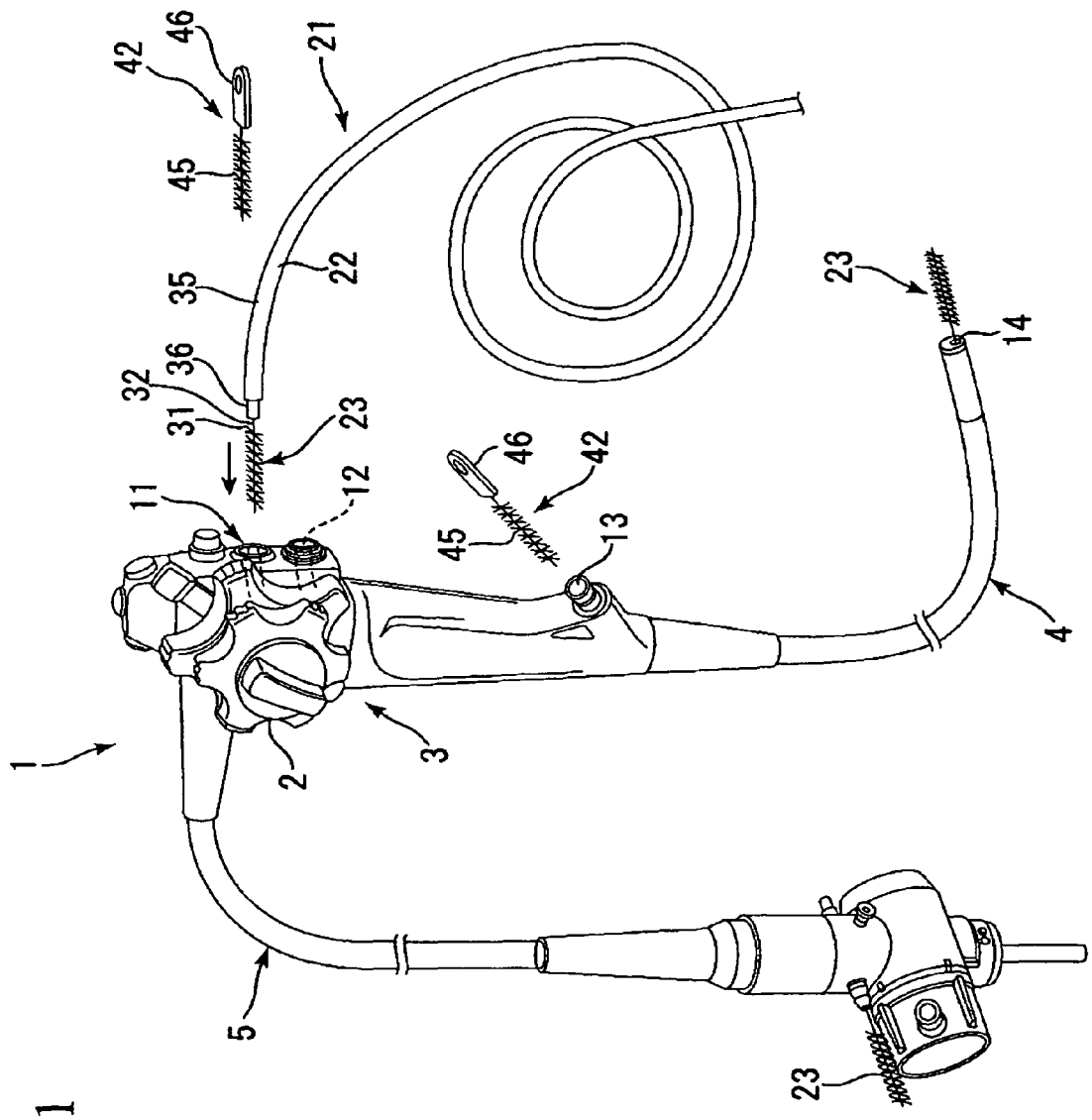
FIG. 1 is a perspective view showing a cleaning brush for an endoscope, and an endoscope to be cleaned, according to a first embodiment of the invention.

The general view of an endoscope 1 is shown in FIG. 1. The endoscope 1 includes an operation part 3 provided with an operating knob 2, etc., an insertion part 4 which has flexibility and is inserted into a body cavity, a universal cord 5 which has a light guide, etc. connected to a light source (not shown), and the like.

Further, this endoscope 1 includes a suction conduit 11, a water feed or air feed conduit 12, a forceps insertion opening 13 that is an example of an opening, and the like. An opening 14 used as a forceps opening or a suction opening is formed at a leading end of the insertion part 4. In order to clean the interior of the suction conduit 11, the water feed or air feed conduit 12, and the like, a cleaning brush 21 for a conduit according to the invention is used.

The cleaning brush 21 includes a shaft 22 which is long and has flexibility, and a brush part 23 provided at a leading end of the shaft 22. As shown in FIG. 2, the brush part 23 includes a plurality of brush bristles 31, a strand 32 twisted across brush bristles 31, and a leading tip 33 attached to leading ends of the strand 32.

The strand 32 is composed of, for example, metal wires such as stainless steel (SUS), which do not rust easily. A trailing end of the strand 32 is fixed to the center of a leading face of the shaft 22 by being screwed into the shaft 22 in its axial direction.

Figure 2:
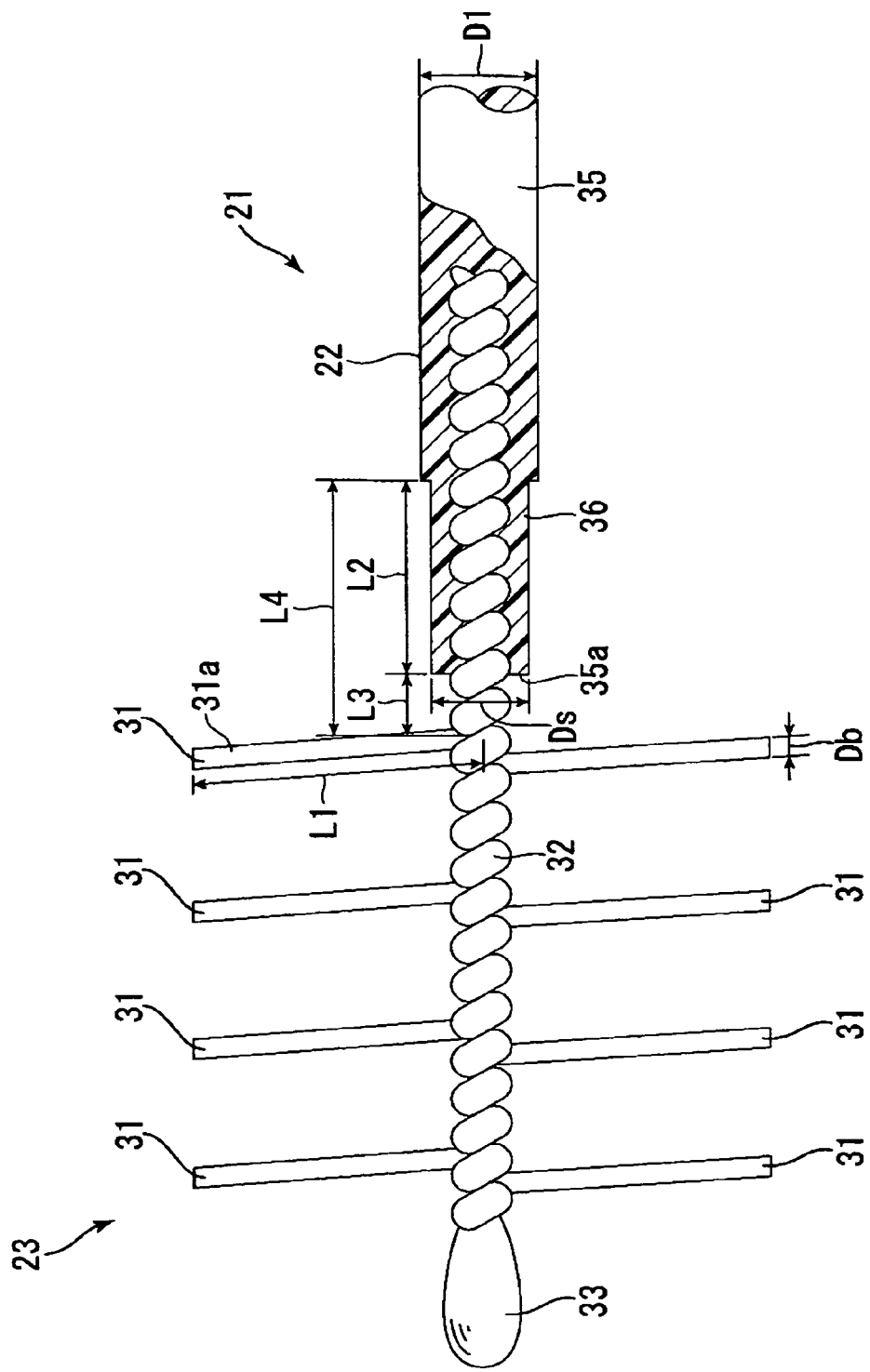
FIG. 2 is a partially cross-sectional side view showing the cleaning brush for an endoscope shown in FIG. 1.

As shown in FIG. 2, the length L1 (length from the center of the strand 32 to the distal end of each of the brush bristles 31) of each of the brush bristles 31 is longer than the radius of a conduit whose internal diameter is the greatest, among conduits of the endoscope 1 for which this cleaning brush 21 is used. For this reason, when the cleaning brush 21 is inserted into a conduit, the distal ends of the brush bristles 31 contact the internal wall of the conduit and elastically deforms along the internal wall of the conduit, so that foreign matter adhering to the internal wall of the conduit can be swept out.

The brush bristles 31 are formed substantially symmetrically in the radial direction of the strand 32 by inserting a number of linear brush bristle materials having a length over twice as large as the length L1 into a pair of wires that is a material for the strand 32, and twisting them. That is, the brush bristles 31 are planted in a cylindrical shape about the strand 32. The brush bristle material includes, for example, synthetic resin, such as polyamide resin represented by nylon.

In the present embodiment, the brush bristles 31 are fixed by sandwiching and twisting the brush bristles 31 while being nipped with the strand 32. However, since it is sufficient if the brush bristles 31 can be fixed in an elastically deformable manner, the fixing means of the brush bristles 31 is not limited. Further, as a means for fixing the strand 32 to the shaft 22, for example, bonding, welding, crimping, etc., and combinations thereof may be used, other than screwing the strand into the end face of the shaft 22 as in the present embodiment.

The leading tip 33 is fixed to the leading ends of the strand 32, that is, the ends thereof opposite to the shaft 22. The material for the leading tip 33 is, for example, a polypropylene resin, and an example of a means for fixing the leading tip to the strand 32 is heat welding. Although the leading tip 33 is not indispensable, the leading tip is used to prevent the leading end of the strand 32 from being peeled off and to prevent the internal wall of a conduit from being damaged.

The shaft 22 is made of a material having flexibility, and integrally has a long shaft body 35 which can be bent along a conduit to be cleaned, and a small diameter part 36 formed at the leading end of the shaft body 35. In a case where the shaft 22 is made of thermoplastic resin, the small diameter part 36 can be molded by molding the leading end of the shaft 22 by a heating mold. Further, the small diameter part 36 may be formed by machining, such as cutting. In this case, chamfering may be performed in order to eliminate a corner of the shaft leading face 35a.

The external diameter D1 of the shaft body 35 is dimensioned such that the cleaning brush can be inserted into a conduit having a smallest diameter, among conduits of the endoscope 1 to be cleaned. If the shaft body 35 becomes too thin, this shaft body becomes not only apt to be buckled when being inserted into a conduit, but also apt to slide due to a small contact surface with a person's fingers. For this reason, it is desirable that the shaft body 35 has strength such that the body is not buckled when being inserted into a conduit, and has the external diameter D1 such that the contact area necessary to grip the shaft body 35 by a person's fingers can be ensured to some extent. That is, it is preferable that the external diameter D1 of the shaft body 35 is dimensioned such that the cleaning brush can be inserted into a conduit having a smallest diameter, but is as thick as possible to that extent.

The external diameter Ds of the small diameter part 36 is smaller than the external diameter D1 of the shaft body 35. Specifically, when the external diameter of the small diameter part 36 is defined as "Ds," the external diameter of one of the brush bristles 31 is defined as "Db," and the internal diameter of a conduit of the endoscope 1 to be cleaned is defined as "Dk" (shown in FIG. 3), the following relationship is satisfied: $Ds+Db \times 2 \leq Dk$. More preferably, the external diameter D1 of the shaft body 35 satisfies the following relationship: $Ds+Db \times 2 \leq D1$.

As shown in FIG. 2, the length L2 of the small diameter part 36 in its axial direction is set such that the length L4 obtained by adding the length L2 and the distance L3 from the position of a root of a brush bristle 31a in a position nearest to the small diameter part 36 to the shaft leading face 35a becomes larger than the length L1 of the brush bristle 31a. Thus, even if the brush bristles 31 are bent laterally toward the shaft 22 when the cleaning brush is inserted into a conduit, the brush bristles 31 touch only the small diameter part 36, but does not touch the shaft body 35. That is, even if the brush bristles 31 overlap the shaft 22, the external diameter of the overlapping portion is smaller than the internal diameter of the conduit.

Next, the operation of the cleaning brush 21 will be described.

Figure 3:
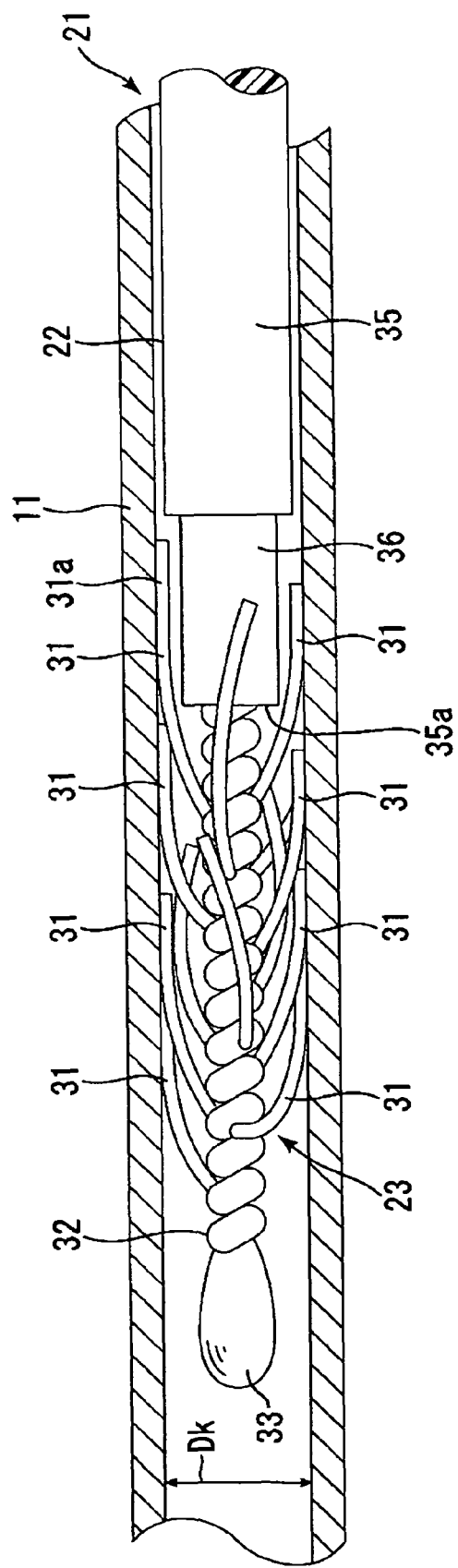
FIG. 3 is a partially cross-sectional side view showing the cleaning brush for an endoscope shown in FIG. 1 which is inserted into a conduit.

When the cleaning brush 21 is inserted into the conduit 11 as shown in FIG. 3, the brush bristles 31 elastically deform along the internal wall of the conduit 11. At this time, although the brush bristles 31 are bent toward the leading face 35a of the shaft body 35, the brush bristles 31 overlap only the small diameter part 36. In the state where the brush bristles 31 have overlapped the small diameter part 36, a total of the external diameter of the small diameter part 36 and twice the external diameter of the brush bristles 31 is smaller than the internal diameter Dk of the conduit 11. For this reason, the resistance generated by the cleaning brush 21 when it is inserted into the conduit 11 does not become large so as to solve the problem that insertion is not allowed.

The length L1 (shown in FIG. 2) of the brush bristles 31 is larger than the radius of a conduit having a largest diameter, among the conduits for which this cleaning brush 21 is used. For this reason, when the cleaning brush is inserted into a conduit irrespective of the internal diameter of the conduit, the brush bristles 31 will be pressed against the internal wall of the conduit. As a result, foreign matter adhering to the internal wall of the conduit can be scraped out.

For this reason, this cleaning brush 21 can cleanse conduits having a wide range of internal diameters from a thin conduit having an internal diameter close to the external diameter of the shaft body 35 to a thick conduit. The strand 32 is hard compared with the shaft 22. However, by shortening the portions consisting only of the strand 32 from the leading face 35a of the shaft 22 to the brush part 23, the cleaning brush can also be used for cleaning an endoscope conduit which is complicated and has a small radius of curvature. Further, since brush bristles having the same size as conventional ones can be used as the brush bristles 31, a repulsive force does not decrease when the brush bristles 31 hit the internal wall of the conduit, and the capability of removing stains does not decline.

In addition, the direction in which the strand 32 is twisted is desirably a right-handed direction. This is because the force in the right-handed direction is usually apt to be applied to the brush part 23 when stains adhering to the brush part 23, etc. are rubbed and washed with a person's fingers. If the strand 32 is twisted in the right-handed direction, therefore, a torque will be applied to a direction in which the strand 32 is screwed into the shaft 22, and consequently the strand 32 is not slackened.

Next, the cleaning brush 21 according to a second embodiment of the invention will be described with reference to FIG. 4. The cleaning brush 21 of the present embodiment has a tapered small diameter part 36A. Since configurations and operation other than this tapered small diameter part are the same as those of the cleaning brush 21 of the first embodiment, parts common to the first and second embodiments are denoted by the same reference numerals, and descriptions thereof are omitted.

Figure 4:
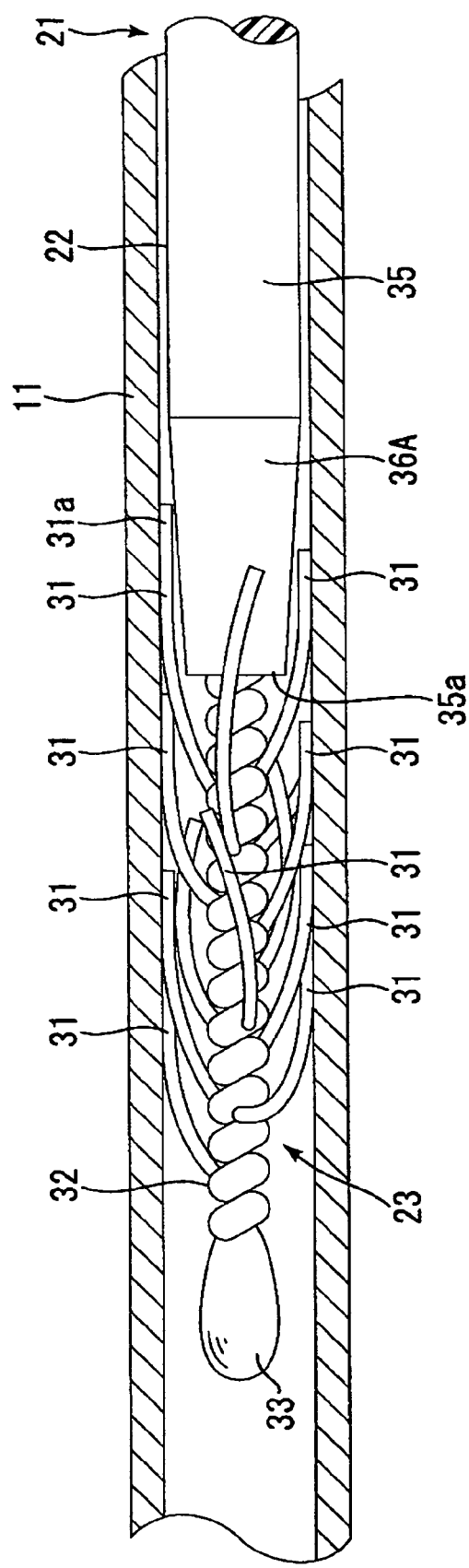
FIG. 4 is a partially cross-sectional side view showing a cleaning brush for an endoscope according to a second embodiment which is inserted into a conduit.

As shown in FIG. 4, the tapered small diameter part 36A has a shape in which the external diameter of the part 36A decreases toward the shaft leading face 35a. When the brush bristle 31a nearest to the shaft leading face 35a is bent toward the shaft 22, a length obtained by adding the external diameter of the small diameter part 36A and twice the external diameter of the brush bristles 31 becomes smaller than the internal diameter of the conduit 11 in a part where the leading end of the brush bristle 31a is located. The tapered small diameter part 36A may be molded by a heating mold similar to the small diameter part 36 of the first embodiment, or may be formed by machining, such as cutting.

Since the cleaning brush 21 with the tapered small diameter part 36A according to the present embodiment does not have a step-like diametral difference between the shaft body 35 and the small diameter part 36A, there is no part where stress concentration is caused as compared with a case where there is a step-like diametral difference. As a result, strength can be increased. Further, since there is no step-like diametral difference, there is no possibility that the cleaning brush may be caught by few convex parts of the internal wall of the conduit 11, and consequently, insertion of the cleaning brush into the conduit 11 can be performed smoothly. In addition, the small diameter part 36A may take a bombshell shape that becomes thin toward the leading end thereof.

Next, a cleaning brush 41 according to a third embodiment of the invention will be described with reference to FIGS. 5 and 6.

The cleaning brush assembly 41 of the present embodiment has the cleaning brush 21 (cleaning brush for a conduit) according to the aforementioned first or second embodiment, and a cleaning brush 42 for an opening suitable for cleaning of an opening that is larger than the cleaning brush 21. In the present embodiment, parts common to those of the cleaning brush 21 of the first or second embodiment are denoted by common reference numerals, and descriptions thereof are omitted. The cleaning brush 42 for an opening is used when cleaning, for example, openings, such as a suction cylinder of the suction conduit 11 and the forceps insertion opening 13 in the endoscope 1 shown in FIG. 1.

Figure 5:
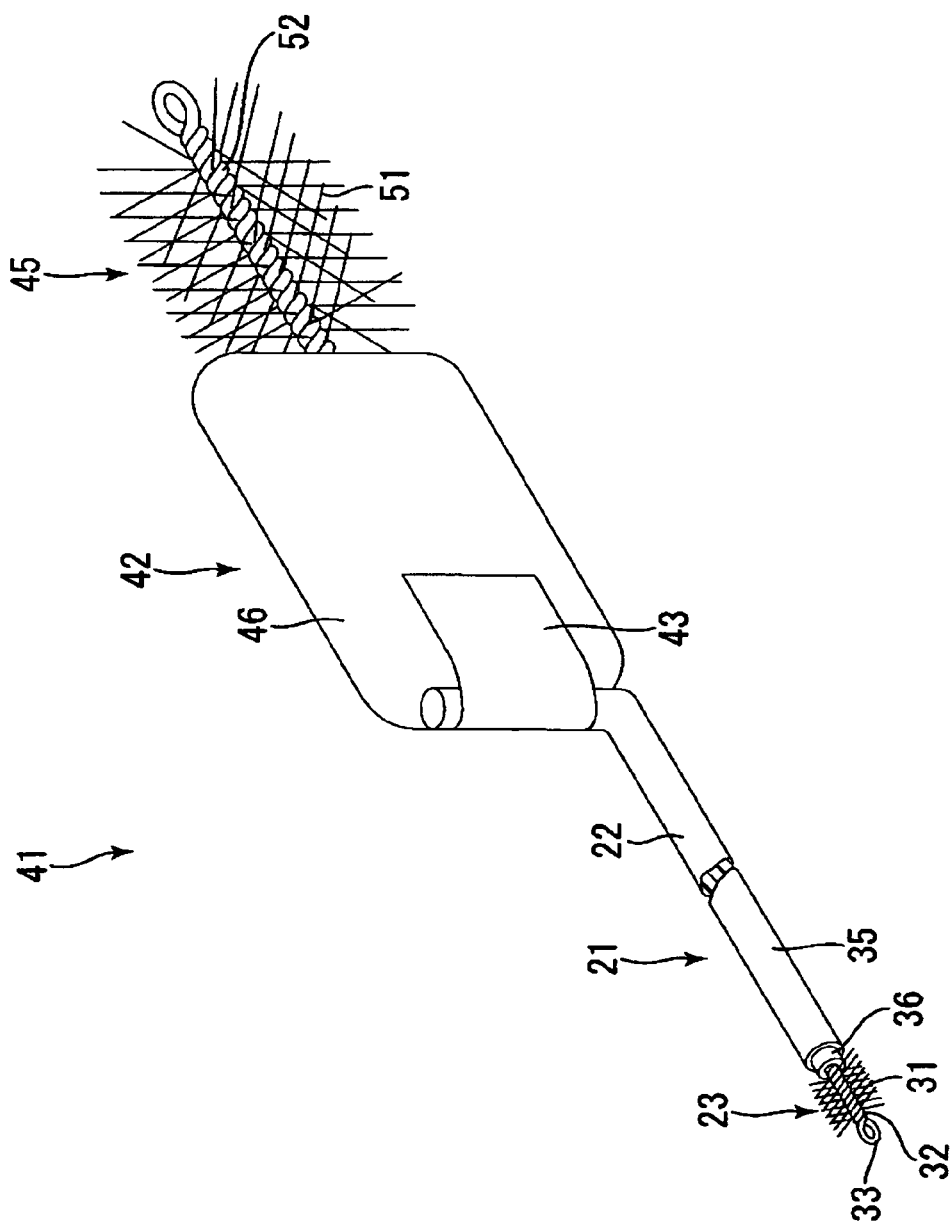
FIG. 5 is a perspective view showing a cleaning brush assembly according to a third embodiment of the invention.

FIG. 5 shows a cleaning brush assembly 41 obtained by combining the cleaning brush 21 for a conduit and the cleaning brush 42 for an opening. The cleaning brush 21 for a conduit and the cleaning brush 42 for an opening are temporarily fixed to each other by a glued tape 43. The cleaning brush 42 for an opening can be separated from the cleaning brush 21 for a conduit, for example, by peeling the glued tape 43 when used. As the glue of the glued tape 43, for example, latex-based water-soluble glues are used.

Figure 6:
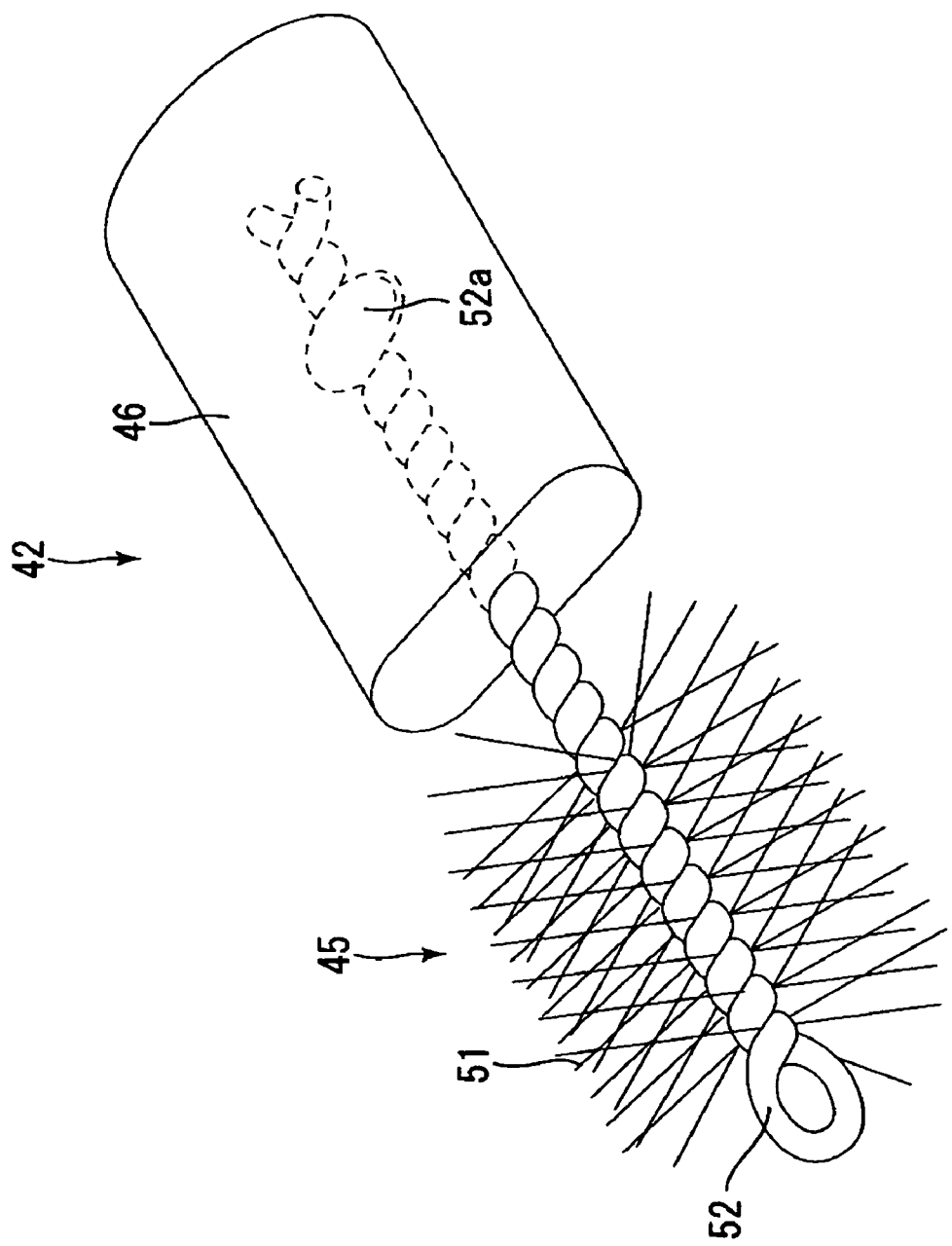
FIG. 6 is a perspective view showing a brush for an opening of the cleaning brush assembly shown in FIG. 5.

As shown in FIG. 6, the cleaning brush 42 for an opening includes a brush part 45, and a shank 46 made of synthetic resin, such as polypropylene. The brush part 45 is composed of a plurality of brush bristles 51 made of, for example, synthetic resin, such as nylon, and a strand 52 consisting of a pair of wires, such as stainless steel. The strand 52 is twisted so as to nip the brush bristles 51. The brush bristles 51 are formed in a cylindrical shape about the strand 52. The shank 46 is formed in a flat shape, and is sized such that it can be gripped with a person's fingers.

A base of the strand 52 is welded and fixed to the shank 46 by insert-molding the base of the strand into the shank 46. A flat part 52a is formed in a part of the strand 52 located inside the shank 46.

The flat part 52a is formed flatly in advance by plastic working, such as press working, before the strand 52 is inserted into the shank 46. Since such a flat part 52a is embedded in the shank 46, even if the cleaning brush 42 for an opening is strongly rotated by a person's fingers when an opening of the endoscope is cleaned, a joined portion between the strand 52 and the shank 46 is prevented from being broken and rotated. For this reason, even if the cleaning brush 42 for an opening is rotated by an excessive force when cleaned, an operation can be performed safely without the possibility of the strand 52 dropping out of the shank 46 or the leading end of the strand 52 being exposed to the outside.

In addition, the size of the flat part 52a of the strand 52 does not need to be considered. In short, it is sufficient if the flat part 52a is sized such that it is received in the shank 46. However, it is necessary that the size of the flat part 52a is above a certain level from the viewpoint of the function of preventing rotation of the flat part with respect to the shank 46.

The operation of the cleaning brush assembly 41 of the present embodiment (FIGS. 5 and 6) will be described below.

In this cleaning brush assembly 41, the cleaning brush 21 for a conduit and the cleaning brush 42 for an opening are connected to each other by the glued tape 43. Thus, when a person in charge of cleaning takes the cleaning brush assembly 41 out of a packaging bag, the cleaning brush 21 for a conduit and the cleaning brush 42 for an opening can be taken out of the bag by one operation.

When the cleaning brush assembly 41 is dipped in cleaning liquid, the glue of the glued tape 43 is dissolved and peeled off, and thereby the cleaning brush 21 for a conduit and the cleaning brush 42 for an opening are separated from each other. Therefore, it is possible to individually use the cleaning brush 21 for a conduit and the cleaning brush 42 for an opening.

For this reason, when the cleaning brush 21 for a conduit is inserted into a conduit of the endoscope 1 (shown in FIG. 1) to clean the conduit, the cleaning brush 42 for an opening does not become a hindrance to cleaning. Further, when an opening of the endoscope 1 is cleaned by the cleaning brush 42 for an opening, the cleaning brush 21 for a conduit does not become a hindrance. Further, in an unused cleaning brush assembly 41, the cleaning brush 21 for a conduit and the cleaning brush 42 for an opening are connected to each other by the glued tape 43. Thus, it can be determined at a glance whether or not the cleaning brush assembly is unused.

Figure 7:
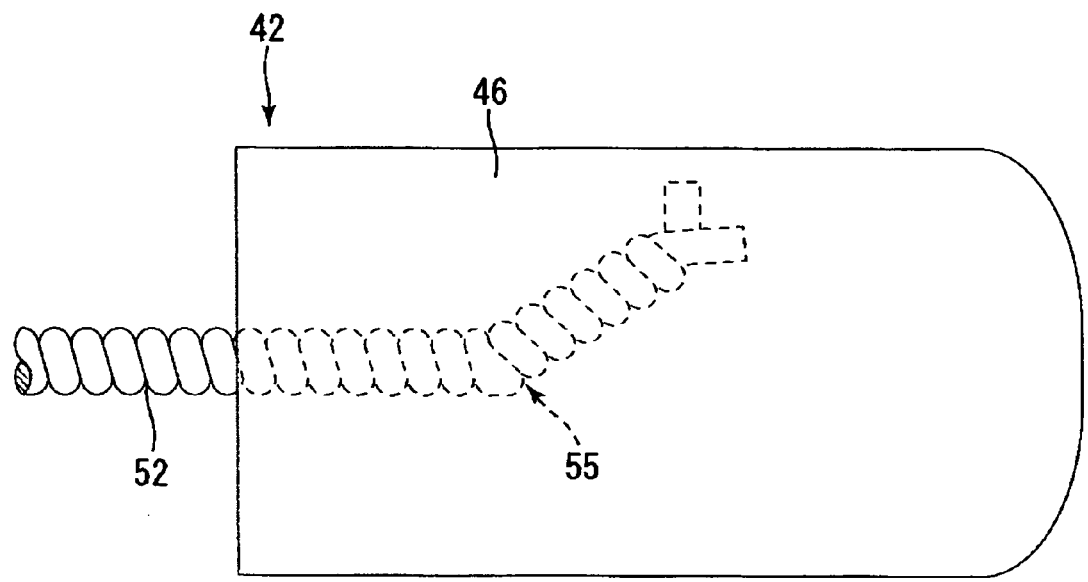
FIG. 7 is a plan view showing a part of a brush for an opening according to a fourth embodiment of the invention.
Figure 8:
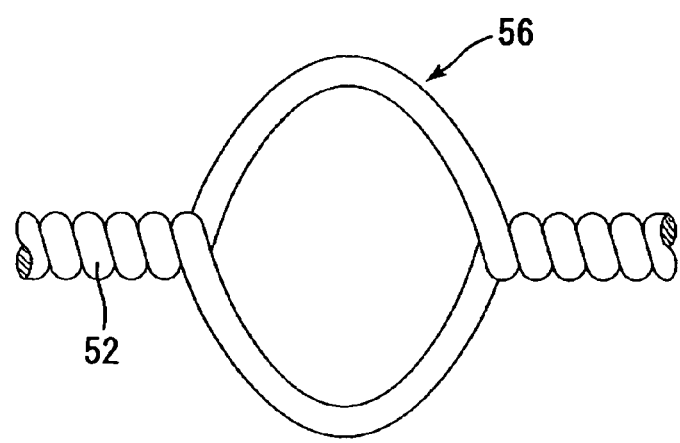
FIG. 8 is a plan view showing a part of a brush for an opening according to a fifth embodiment of the invention.

In the cleaning brush 42 for an opening, the flat part 52a is provided in a part of the strand 52, whereby rotation of the strand 52 with respect to the shank 46 is suppressed. However, in order to achieve the same function, for example, a bent part 55 may be formed at the trailing end of the strand 52 like a fourth embodiment shown in FIG. 7, or a loosened and expanded part 56 may be formed in a part of the strand 52 like a fifth embodiment shown in FIG. 8.

Figure 9:
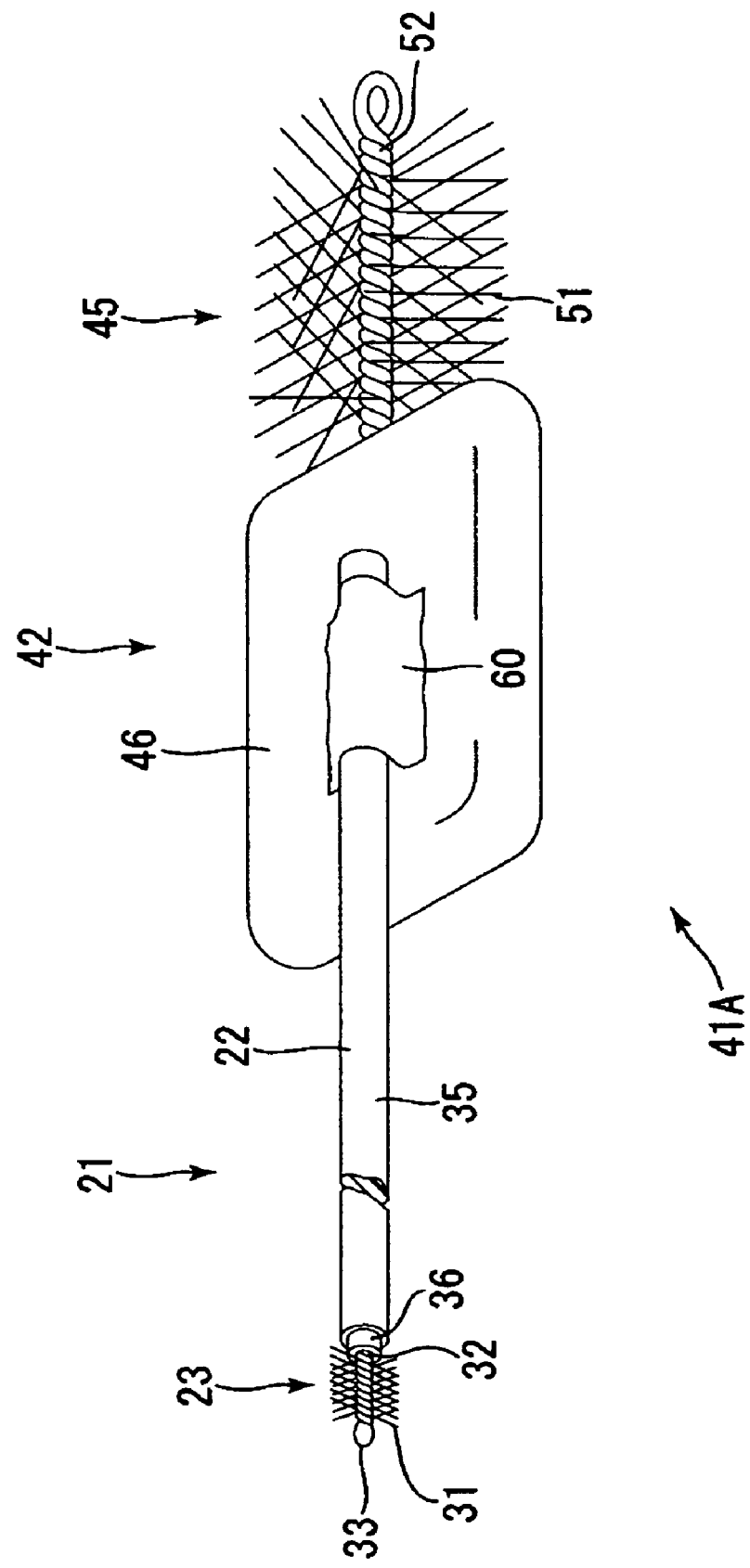
FIG. 9 is a perspective view showing a cleaning brush assembly according to a sixth embodiment of the invention.

Further, as a means for connecting the cleaning brush 21 for a conduit and the cleaning brush 42 for an opening to each other, instead of using the glued tape 43, the cleaning brush 42 for an opening may be directly connected to an end of the shaft 22 of the cleaning brush 21 for a conduit with adhesive 60 that is dissolved in water after being dried, like the cleaning brush assembly 41A of a sixth embodiment shown in FIG. 9.

Figure 10:
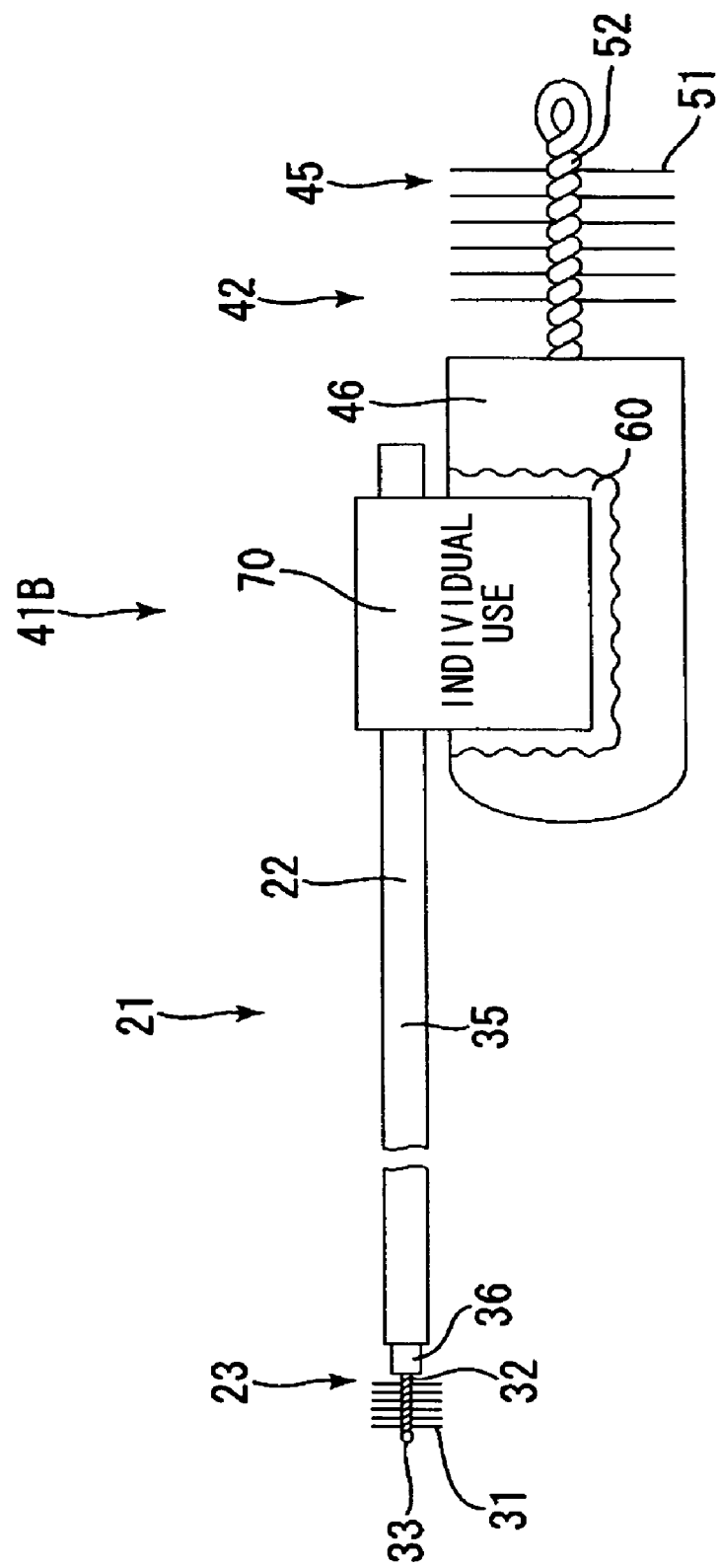
FIG. 10 is a side view showing a cleaning brush assembly according to a seventh embodiment of the invention.
Figure 11:
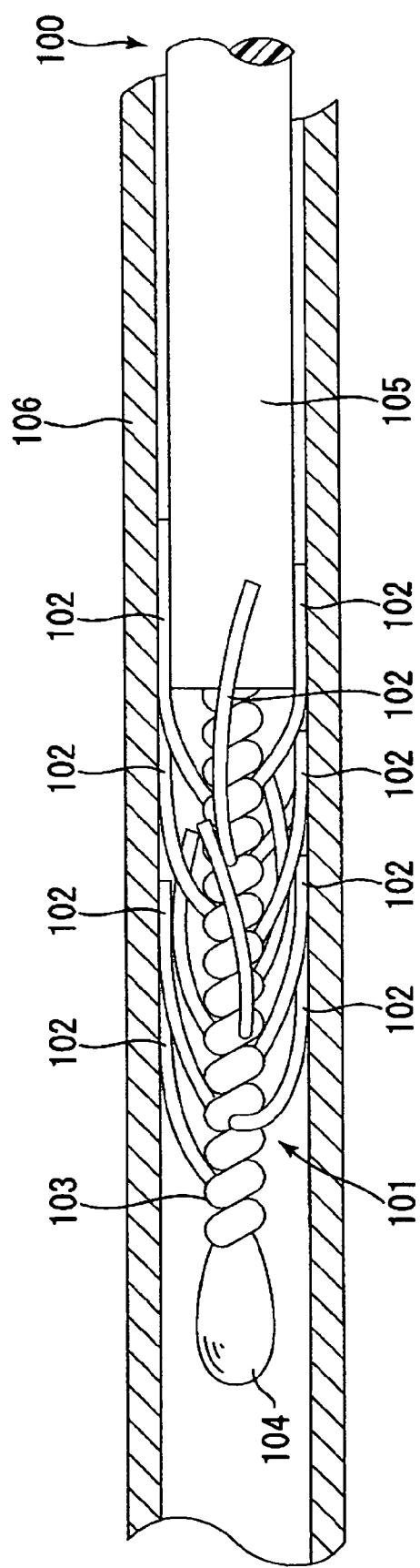
FIG. 11 is a partially cross-sectional side view showing a conventional cleaning brush for an endoscope which is inserted into a conduit.

Otherwise, like the cleaning brush assembly 41B of a seventh embodiment shown in FIG. 10, a plate member 70 for displaying a warning, etc. may be welded to the end of the shaft 22 of the cleaning brush 21 for a conduit so as to cover an end of the shaft 22. The plate member 70 and the shank 46 of the cleaning brush 42 for an opening may be connected to each other with adhesive 60 that is easily dissolved in water after being dried. In addition, in these embodiments, parts common to those of the above embodiments (FIGS. 1 to 9) are denoted by the same reference numerals, and descriptions thereof are omitted.

INDUSTRIAL APPLICABILITY

According to the cleaning brush of the invention, even when a thin conduit having an internal diameter close to the external diameter of a shaft is cleaned, cleaning can be performed without increasing insertion resistance and without causing problems that insertion becomes difficult or insertion is not allowed. Further, according to the invention, conduits having a wide range of internal diameters from a thin conduit having an internal diameter close to the external diameter of the shaft to a thick conduit having a sufficiently larger internal diameter than the external diameter of the shaft can be cleaned. Further, the cleaning brush is also suitable for cleaning of an endoscope conduit that is complicated and has a small radius of curvature, and has no decline in the capability of removing stains compared with a conventional brush.

The invention claimed is:

1. A cleaning brush assembly comprising:
   a cleaning brush which is inserted into a conduit to be cleaned, the cleaning brush comprising a long and flexible shaft, and a brush part provided at a leading end of the shaft and having brush bristles for cleaning the inside of a conduit, the shaft including a small diameter part smaller in external diameter than other part of the shaft, and the small diameter part being located at a position overlapped with the brush bristles bent toward the leading end of the shaft; and
   an opening brush suitable for cleaning an opening having a larger diameter than the conduit, the opening brush comprising a shank and a strand having a twisted portion and a flat part, the twisted portion including a pair of wires twisted with each other and being embedded in the shank, the flat part being formed flatly and being embedded in the shank, a size of the flat part being larger than the twisted part.

2. The cleaning brush assembly according to claim 1, wherein, where an external diameter of the small diameter part is defined as "Ds," an external diameter of one of the brush bristles is defined as "Db," and an internal diameter of the conduit is defined as "Dk," the following formula is satisfied:

$$Ds+Db \times 2 \geq Dk.$$

3. The cleaning brush assembly according to claim 1, wherein, where an external diameter of the small diameter part is defined as "Ds," an external diameter of one of the brush bristles is defined as "Db," and an external diameter of the other parts of the shaft is defined as "D1," the following formula is satisfied:

$$Ds+Db \times 2 \leq D1.$$

4. The cleaning brush assembly according to claim 1, wherein a length obtained by adding a length of the small diameter part in its axial direction and a distance from a root of a brush bristle in a position nearest to the small diameter part to a leading face of the shaft is set larger than a length of the brush bristle.

5. The cleaning brush assembly according to claim 1, wherein the small diameter part has a tapered shape, and an external diameter of the small diameter part decreases toward a leading face of the shaft.

6. The cleaning brush assembly according to claim 1, wherein the cleaning brush used for a conduit and the opening brush are connected to each other when unused.

7. The cleaning brush assembly according claim 1, wherein, where a length of a brush bristle in a position nearest to the small diameter part among the brush bristles is defined as "L1," a length of the small diameter part in an axial direction thereof is defined as "L2," and a distance from a position of a root of the brush bristle in the position nearest to the small diameter part to a leading face of the shaft is defined as "L3," the following formula is satisfied:

$$L3 < L2 < L1 < L2+L3.$$

* * * * *